United States Patent [19]
Elsberry et al.

[11] Patent Number: 5,798,114
[45] Date of Patent: Aug. 25, 1998

[54] REFILLABLE BODY POWERED DRUG DELIVERY TECHNIQUES

[75] Inventors: Dennis D. Elsberry, New Hope; Robert E. Kim, Shoreview, both of Minn.

[73] Assignee: Medtronic Incorporated, Minneapolis, Minn.

[21] Appl. No.: 640,360

[22] Filed: Apr. 30, 1996

[51] Int. Cl.$^6$ .................................. A61F 2/02; A61K 9/22
[52] U.S. Cl. .......................................... 424/423; 604/892.1
[58] Field of Search ........................ 424/423; 604/892.1

[56] References Cited

U.S. PATENT DOCUMENTS

| | | |
|---|---|---|
| 4,160,754 | 7/1979 | Shapel et al. . |
| 4,624,827 | 11/1986 | Ayer et al. . |
| 5,034,229 | 7/1991 | Magruder et al. . |
| 5,057,318 | 10/1991 | Magruder et al. . |
| 5,059,423 | 10/1991 | Magruder et al. . |
| 5,110,596 | 5/1992 | Magruder et al. . |
| 5,135,523 | 8/1992 | Magruder et al. . |
| 5,169,390 | 12/1992 | Athayde et al. .......................... 604/141 |
| 5,174,999 | 12/1992 | Magruder et al. . |
| 5,320,616 | 6/1994 | Magruder et al. . |

OTHER PUBLICATIONS

Osade et al., "Shape Memory in Hydrogels", *Nature*,. 376:219 (1995).
Alzet Technical Information Manual, Alze Corporation (Dec. 1991).

*Primary Examiner*—Carlos Azpuru
*Attorney, Agent, or Firm*—Banner & Witcoff Ltd.

[57] ABSTRACT

Techniques for implanting and refilling a device for delivering a treatment agent to a body. First and second chambers for holding treatment agent and delivery agent, respectively, are placed adjacent docking compartments adapted to receive a hypodermic needle through septums so that the expended delivery agent can be withdrawn and a new supply of treatment agent can be introduced without removing the device from its implanted position in a body.

31 Claims, 4 Drawing Sheets

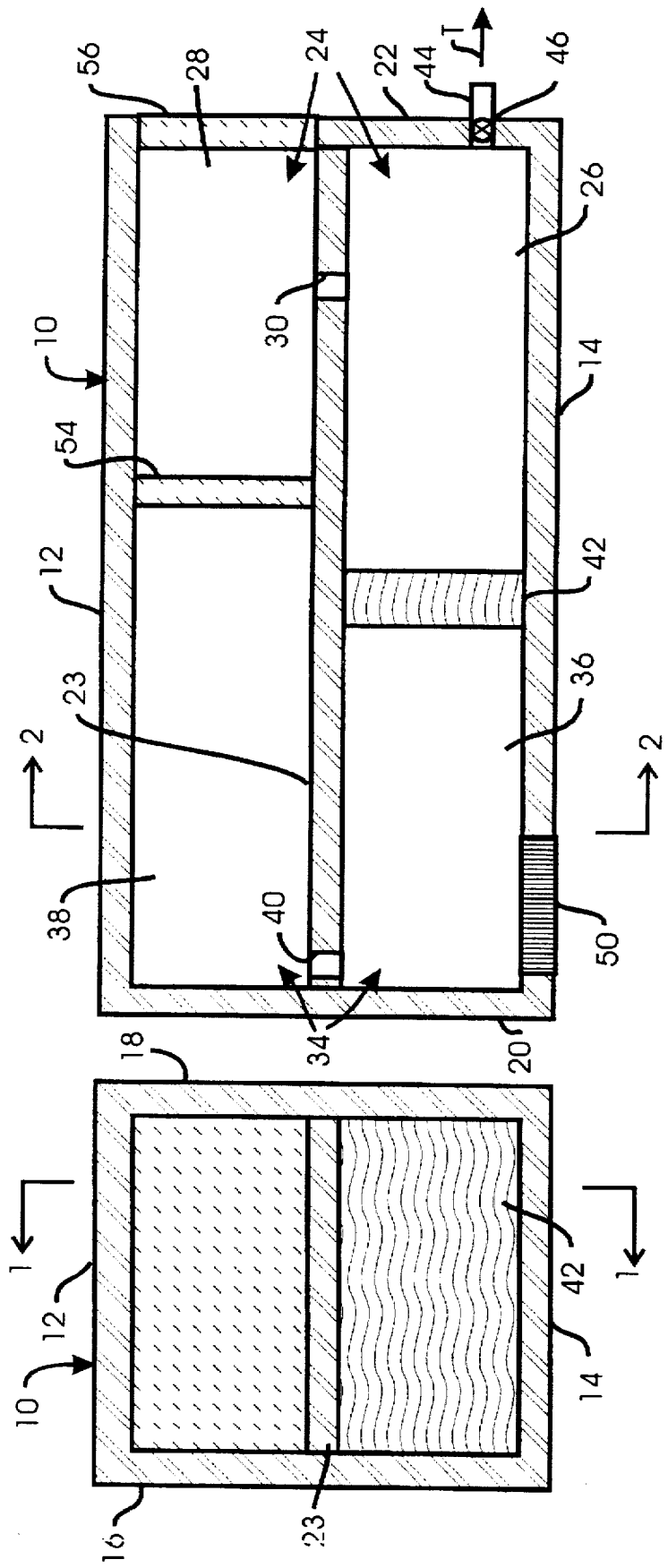

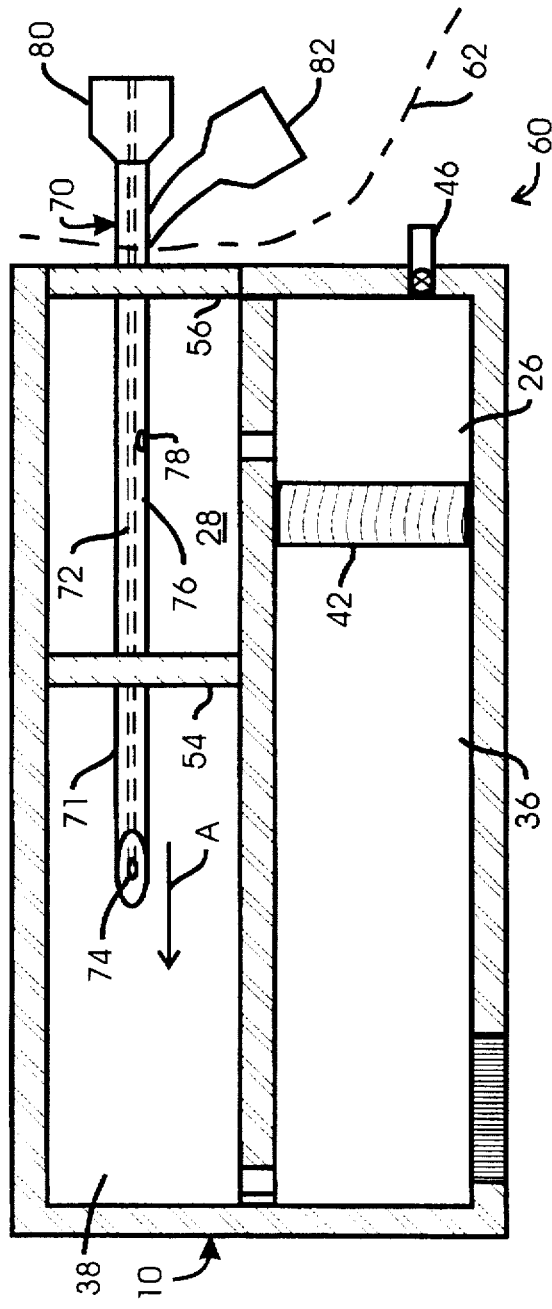
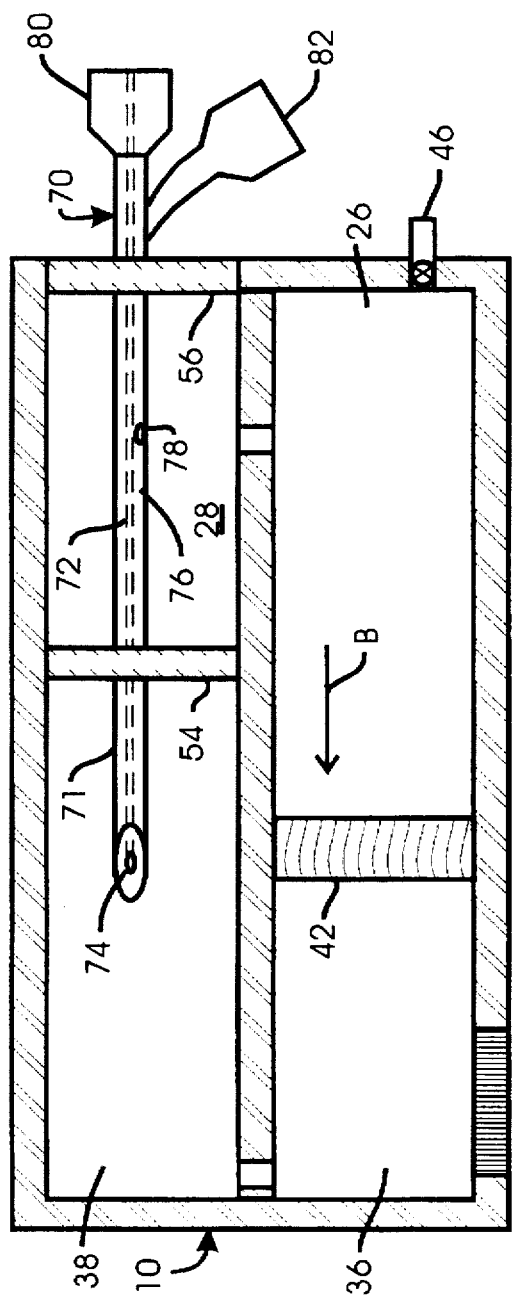

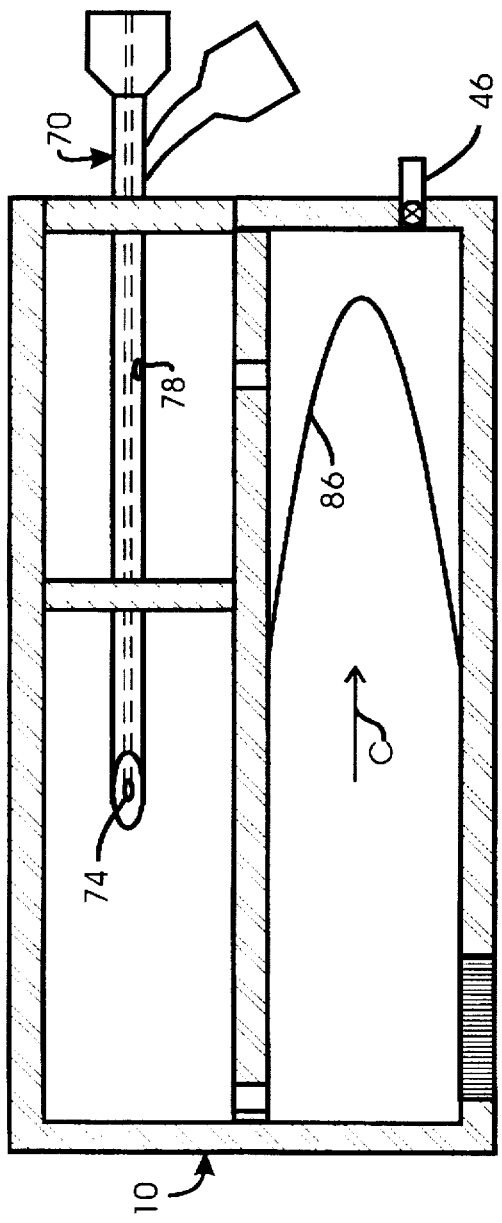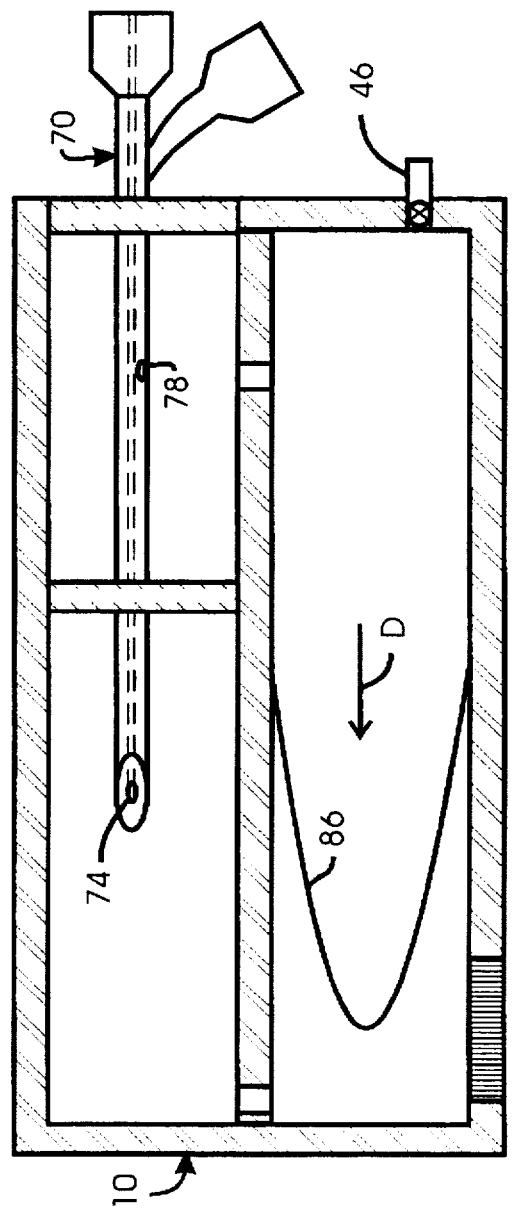

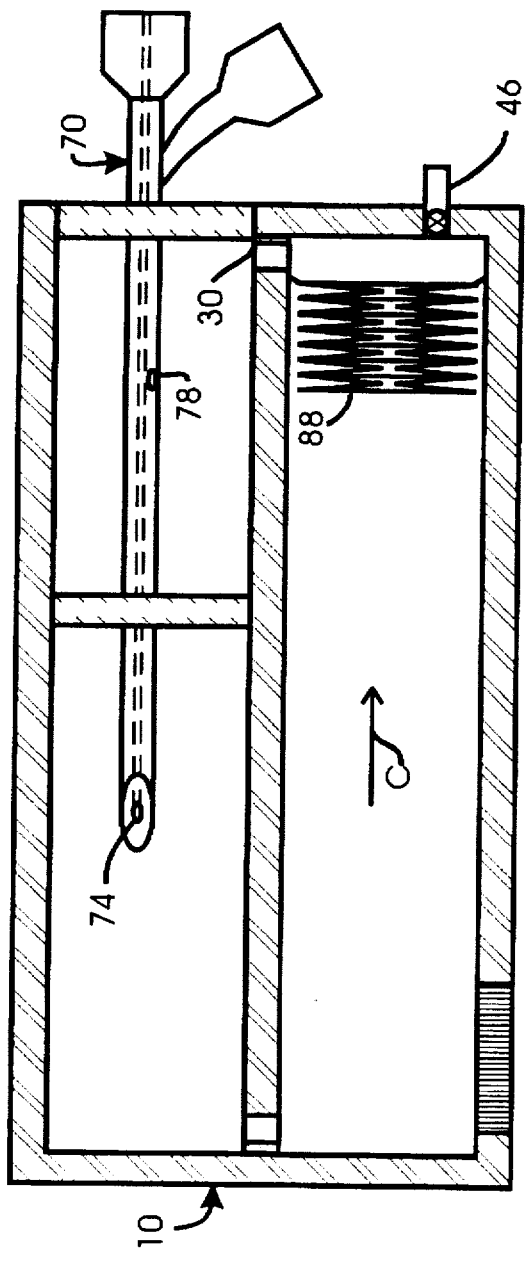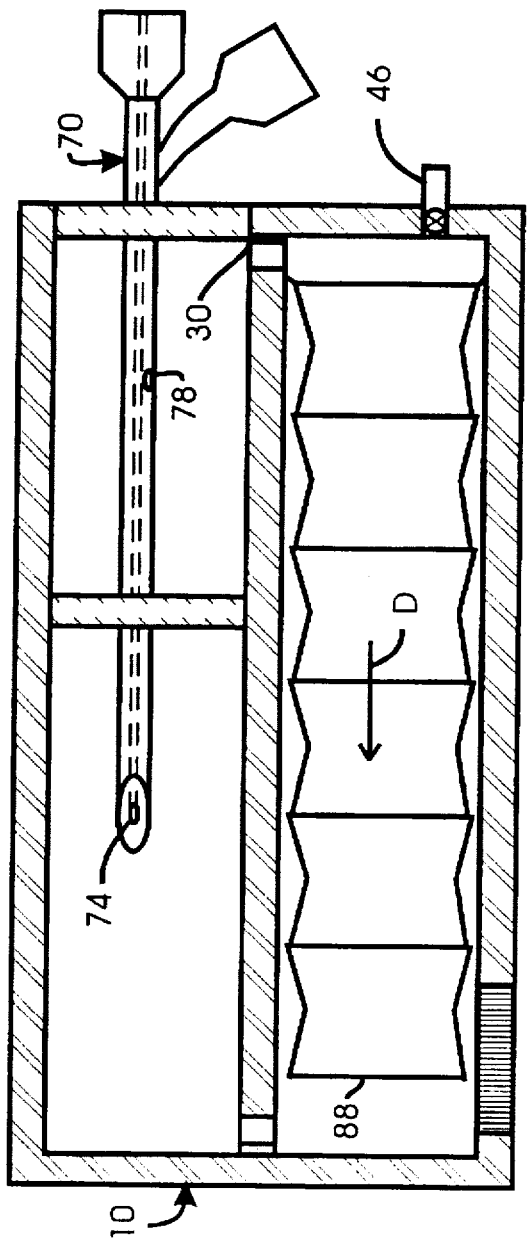

REFILLABLE BODY POWERED DRUG DELIVERY TECHNIQUES

BACKGROUND OF THE INVENTION

1. Field of the Invention

This invention relates to implantable drug delivery techniques, and more particularly relates to such techniques in which fluid from a body is used to provide a force which delivers a treatment agent.

2. Description of Related Art

Drug delivery systems based on osmotic pumps are known and are described, for example, in U.S. Pat. No. 4,624,847 (Ayers et al.) issued Nov. 25, 1986. When using such an osmotic pump, once the hydration of the osmotic medium has occurred, it is difficult, if not impossible, to rejuvenate the medium. Experience also has shown that it is difficult, if not impossible, to replace the treatment agent that is distributed by the osmotic pressure. This invention addresses these problems.

SUMMARY OF THE INVENTION

The invention is useful in an implantable and refillable dispensing device for delivering a treatment agent, such as drug, to a body of a human patient or animal. In such an environment, the invention preferably comprises a first chamber for holding the treatment agent and a second chamber for holding a delivery agent. A conduit extends between the first chamber and the body. Pressure is applied to the first chamber due to changes in volume of the delivery agent in the second chamber, so that the treatment agent is delivered through the conduit to the body. Septum means separate the first chamber from the second chamber and separate the device from the body. By using these techniques, the treatment agent can be resupplied into the first chamber and the hydrated delivery fluid can be withdrawn from the second chamber without removing the device from the body.

According to a preferred embodiment, a hypodermic needle is received through the skin of the body and the septum means into the first chamber in order to administer a new supply of treatment agent. The hypodermic needle also may enter the second chamber through the septum means in order to withdraw the hydrated delivery agent. By using a hypodermic needle with two lumens, the new supply of treatment agent may be delivered at the same time that the hydrated delivery agent is removed. The hypodermic needle is withdrawn after the device is rejuvenated and the septum means automatically seals the entry point of the hypodermic needle so that the device may continue to deliver the treatment agent to the body.

By using the foregoing techniques, drug dispensing devices utilizing osmotic pressure may be used over extended periods of time with a degree of effectiveness unattainable by prior art techniques.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 1 is a cross-sectional diagrammatic view of a preferred form of dispensing device made in accordance with the present invention taken along line 1—1 of FIG. 2;

FIG. 2 is a cross-sectional diagrammatic view of the dispensing device shown in FIG. 1 taken along line 2—2 of FIG. 1;

FIG. 3 is a cross-sectional view like FIG. 1 illustrating the insertion of a dual lumen hypodermic needle into the device after the supply of delivery agent is reduced;

FIG. 4 is a cross-sectional view like FIG. 3 showing the device after rejuvenation;

FIG. 5 is a cross-sectional view like FIG. 3 showing an alternative embodiment of the invention before rejuvenation;

FIG. 6 is a cross-sectional view like FIG. 5 showing the alternative embodiment after rejuvenation;

FIG. 7 is a cross-sectional view like FIG. 5 showing an alternative embodiment prior to rejuvenation; and FIG. 8 is a cross-sectional view like FIG. 7 showing the alternative embodiment after rejuvenation.

DESCRIPTION OF THE PREFERRED EMBODIMENTS

Referring to FIGS. 1 and 2, a preferred form of implantable device 10 made in accordance with the invention includes a top wall 12, a bottom wall 14, side walls 16 and 18, and end walls 20 and 22. An interior wall 23 separates device 10 into various chambers and compartments.

For example, a chamber for holding a treatment agent 24, such as a drug, includes a main chamber 26 and a docking compartment 28 that are coupled through a conduit 30. A chamber 34 for holding a delivery agent responsive to osmotic pressure includes a main chamber 36 and a docking compartment 38 that are coupled by a conduit 40. Chambers 26 and 36 are separated by a moveable plunger 42 that can move to the right or the left as shown in FIG. 1 in response to fluid pressure.

A conduit 44, including a one-way valve 46, delivers a treatment agent in the direction shown by arrow T. A semi-permeable membrane 50 enables body fluid to enter chamber 36, thereby pushing plunger 42 to the right and delivering a dosage of treatment agent to a body through one-way valve 46 in the direction of arrow T.

A septum 54 divides compartments 28 and 38, and a septum 56 divides device 10 in general, and compartment 28 in particular, from a surrounding body in which device 10 may be implanted.

Still referring to FIG. 1, compartment 36 may hold a variety of different delivery agents. For example, chamber 36 may hold a hydrophilic medium such as polyacrylic and polymethacrylic copolymer hydrogels with or without quaternary anions. Such a hydrophilic medium is available from B.F. Goodrich and Rohm Tech companies under the trademark Carbopol® and EUDRAGIT®. Such hydropolymers are capable of swelling or expanding usually from 2–50 times in volume through imbibition of water.

Chamber 36 also may hold an osmotic agent, such as a solution of sodium chloride and water. Alternatively, chamber 36 may hold a hydrophilic polymer (e.g., hydrogel) having a composition such that as hydration occurs, the material swells creating a displacement force which applies pressure to plunger 42, and urges the plunger in the direction of arrow T. Such hydrogels are known and have been used to form stomal seals. In addition, such hydrogels have been recently reported by German scientists in U.S. Pat. No. 4,160,754, which describes polymer gels having molecular weights ranging from 200–100,000 containing at least one ether, thioether, acetal ester, urethane and/or carbonate group. Further polymer gels capable of reversible shape modification in respect to external factors, (i.e., temperature, pH, electrical field), have been reported by Osada and Matsuda, in *Nature* 376:219, 1995.

Referring to FIG. 3, device 10 is implantable in a body 60 of an animal or human having a skin 62. Initially, before being implanted, chamber 36 is filled with a delivery agent and chamber 26 is filled with a treatment agent, such as a drug. Treatment agents suitable for use in device 10 include opiods (i.e., morphine, hydromorphone, fentanyl, sufentanil), local anesthetics (i.e., bupivacaine, tetracaine, lidocaine), antispasticity agents (i.e., baclofen, diazepam, tizanidine, clonidine), antineoplastics (i.e., floxuridine, 5-FU, methotrexate, doxorubicin, novatrone), neurotrophins (i.e., NGF, NT-3, BDNF, CNTF, GDNF), anti-inflammatory agents (i.e., dexamethasone, hydrocortisone, NSAIDS).

Due to osmotic pressure of the fluid in body 60, body fluid enters semi-permeable membrane 50 and increases the volume of fluid in chamber 36 so that plunger 42 is moved to the right, thereby administering drug to the body through conduit 46. After a substantial portion of the treatment agent has been delivered, plunger 42 may be, for example, in the position shown in FIG. 3. In order to rejuvenate the device, fluid must be withdrawn from chamber 36 and a new supply of treatment agent must be introduced into chamber 26. Rejuvenation is achieved by inserting a dual-lumen hypodermic needle 70 through skin 62 and through septums 56 and 54 in the direction of arrow A.

Hypodermic needle 70 includes an outer cylindrical surface 71 and defines a center lumen 72 that can draw fluid through an end-hole 74. Needle 70 also defines an outer lumen 76 located outside lumen 72 and within surface 71 that defines an exit hole 78. A vacuum connector 80 allows a vacuum source to be connected to the center lumen 72, thereby drawing fluid from chamber 36 and compartment 38 through needle 70. A drug supply connector 82 enables a treatment agent to be introduced through outer lumen 76 and hole 78 into compartment 28 and chamber 26. As the rejuvenation process continues, plunger 42 is moved to the left as shown in FIG. 4 as the volume of treatment agent in chamber 26 increases and places pressure on plunger 42 in the direction of arrow B. After chamber 26 is filled with a drug agent, hypodermic needle 70 is removed. The septums are made from a self-sealing material that seals the puncture holes made in them by hypodermic needle 70. Exemplary septums may be made from the following materials: polysiloxane elastomer, fluoroelastomer, and composite elastomers of polyfluorosilicone which exhibit excellent sealing characteristics to multiple perforations.

FIGS. 5 and 6 show an alternative embodiment of device 10 which substitutes a plastic sheet 86 in place of plunger 42. Referring to FIG. 5, due to osmotic pressure, chamber 36 gradually fills with fluid and urges sheet 86 in the direction of arrow C, thereby delivering treatment agent through conduit 46. Device 10 is rejuvenated in the same manner described in connection with FIGS. 3 and 4 by hypodermic needle 70. As the supply of the drug agent is replenished in chamber 26 and the fluid in chamber 36 is withdrawn, sheet 86 is urged in the direction of arrow D and eventually assumes the shape shown in FIG. 6. After chamber 26 is refilled with treatment agent, hypodermic needle 70 is withdrawn in the same manner described in connection with FIGS. 3 and 4.

Sheet 86 may be fabricated from the following materials: polyvinyl chloride, copolymers of polyvinyl chloride with vinylidene chloride, polyether urethanes, and polyamide polymers to fabricate a flexible sheet for drug containment.

A sheet 88 could be fabricated from a metal alloy, i.e., titanium, to provide a bellows as shown in FIG. 7 and 8. Bellows 88 operates in a manner similar to sheet 86.

By using the foregoing techniques, an implantable device that operates on osmotic pressure can be rejuvenated without withdrawing the device from a body in which it is implanted, thereby extending its life and providing drug treatment with a reliability and longevity unattainable by prior art techniques.

Those skilled in the art will recognize that the preferred embodiments may be altered or amended without departing from the true spirit and scope of the invention, as defined in the accompanying claims.

We claim:

1. An implantable and refillable dispensing device for delivering a treatment agent to a body comprising in combination:

a first chamber for holding said treatment agent;

a conduit between said first chamber and said body;

a second chamber for holding a delivery agent;

means for applying pressure to said first chamber due to changes in volume of said delivery agent in said second chamber so that said treatment agent is delivered through said conduit to said body;

septum means for facilitating the introduction of treatment agent into said first chamber and for facilitating the removal of delivery agent from said second chamber, whereby said treatment agent can be introduced into said first chamber and said delivery fluid can be withdrawn from said second chamber using a rejuvenating device, while said dispensing device remains implanted in the body.

2. A device, as claimed in claim 1, wherein said treatment agent comprises a drug.

3. A device, as claimed in claim 1, wherein said conduit comprises a one way valve.

4. A device, as claimed in claim 1, wherein said delivery agent comprises a hydrophilic medium.

5. A device, as claimed in claim 1, wherein said delivery agent comprises a sodium chloride solution.

6. A device, as claimed in claim 1, wherein said delivery agent comprises a hydrophilic hydropolymer.

7. A device, as claimed in claim 1, wherein said means for applying pressure comprises a plunger.

8. A device, as claimed in claim 1, wherein said means for applying pressure comprises an impermeable plastic sheet.

9. A device, as claimed in claim 1, wherein said septum means comprises a first septum for separating said first chamber from said second chamber and a second septum for separating said device from said body.

10. A device, as claimed in claim 9, wherein said first chamber comprises a first docking compartment, and wherein said second chamber comprises a second docking compartment, and wherein said first septum separates said first docking compartment from said second docking compartment, wherein said second septum separates said first docking compartment from said body, and wherein said first and second septums are aligned whereby said treatment agent can be introduced into said first chamber and said delivery fluid can be withdrawn from said second chamber by one or more hypodermic needles without removing said device from said body.

11. A device, as claimed in claim 10, wherein said hypodermic needle comprises a first lumen and a second lumen, wherein said first lumen is coupled to said first docking compartment, wherein said second lumen is coupled to said second docking compartment and wherein said first septum separates said first and second lumens.

12. A device, as claimed in claim 1, wherein said means for applying pressure comprise a bellows.

13. A dispensing device for delivering a treatment agent to a body comprising:

a treatment agent chamber for holding the treatment agent;

a delivery agent chamber for holding a supply of delivery agent;

a conduit for permitting egress of the treatment agent from the treatment agent chamber to the body;

means for applying pressure to the treatment agent chamber due to changes in volume of the delivery agent in the delivery agent chamber so that the treatment agent is delivered through the conduit to the body; and a first septum for permitting a rejuvenating device to selectively communicate with the treatment agent chamber to supply treatment agent thereto.

14. The device according to claim 13, further comprising a second septum for permitting a rejuvenating device to selectively communicate with the delivery agent chamber to remove delivery agent therefrom.

15. The device according to claim 13, wherein the first septum partially separates the treatment agent chamber from the delivery agent chamber.

16. The device according to claim 13, wherein the means for applying pressure comprises a movable plunger.

17. The device according to claim 13, wherein the means for applying pressure comprises a bellows.

18. The device according to claim 13, wherein the means for applying pressure comprises a plastic sheet.

19. The device according to claim 13, further comprising a semi-permeable membrane for permitting ingress of fluid from the body to the delivery agent chamber.

20. The device according to claim 14, wherein at least one of the first septum and the second septum is comprised of a self-sealing material.

21. The device according to claim 14, wherein at least one of the first septum and the second septum is comprised of a material selected from the group consisting of polysiloxane elastomer, fluoroelastomer or composite elastomers of polyfluorosilicone.

22. An implantable dispensing device for deliverying a treatment agent to a body comprising:

a main chamber including a treatment agent chamber for containing a treatment agent and a delivery agent chamber for containing delivery agent;

a conduit for permitting egress of treatment agent from the treatment agent chamber to the body;

means for applying pressure to the treatment agent chamber due to changes in volume of the delivery agent in the delivery agent chamber so that the treatment agent is delivered through the conduit to the body; and a docking compartment, in communication with the main chamber, for facilitating selective communication of the treatment agent chamber and the delivery agent chamber with a rejuvenating device adapted to remove a supply of exhausted delivery agent from the delivery agent chamber and to introduce a fresh supply of treatment agent to the treatment agent chamber.

23. The device according to claim 22, wherein the docking compartment comprises a first septum for permitting selective communication of the delivery agent chamber with the rejuvenating device.

24. The device according to claim 23, wherein the docking compartment includes a second septum for permitting selective communication of the treatment agent chamber with the rejuvenating device.

25. The device according to claim 23, wherein the first septum partially separates the treatment agent chamber from the delivery agent chamber.

26. The device according to claim 22, wherein the means for applying pressure comprises a plunger movably mounted within the main chamber.

27. The device according to claim 22, wherein the means for applying pressure comprises an expansible bellows disposed in the main chamber.

28. The device according to claim 22, wherein the means for applying pressure comprises a plastic sheet disposed in the main chamber.

29. The device according to claim 22, further comprising a semi-permeable membrane for permitting ingress of fluid from the body to the delivery agent chamber.

30. The device according to claim 24, wherein at least one of the first septum and the second septum is comprised of a self-sealing material.

31. The device according to claim 24, wherein at least one of the first and second septum is comprised of a material selected from the group consisting of polysiloxane elastomer, fluoroelastomer or composite elastomers of polyfluorosilicone.

* * * * *